(12) United States Patent
Ryu

(10) Patent No.: US 7,737,075 B2
(45) Date of Patent: *Jun. 15, 2010

(54) NI CATALYST, PROCESS FOR MAKING CATALYSTS AND SELECTIVE HYDROGENATION PROCESS

(75) Inventor: J. Yong Ryu, League City, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/950,936

(22) Filed: Dec. 5, 2007

(65) Prior Publication Data

US 2008/0119354 A1    May 22, 2008

Related U.S. Application Data

(62) Division of application No. 10/828,823, filed on Apr. 21, 2004, now Pat. No. 7,408,089.

(60) Provisional application No. 60/554,627, filed on Mar. 19, 2004.

(51) Int. Cl.
  *B01J 23/00* (2006.01)
  *B01J 21/00* (2006.01)
  *B01J 20/00* (2006.01)
(52) U.S. Cl. ............... 502/315; 502/259; 502/314; 502/327; 502/328; 502/329; 502/330; 502/331; 502/332; 502/335; 502/337; 502/355; 502/407; 502/415; 502/439
(58) Field of Classification Search ............... 502/245, 502/252, 259, 301, 313, 314, 315, 327, 328, 502/329, 330, 331, 332, 335, 337, 355, 407, 502/415, 439
See application file for complete search history.

(56) References Cited

U.S. PATENT DOCUMENTS

| | | | | |
|---|---|---|---|---|
| 2,620,314 | A | | 12/1952 | Hoekstra et al. |
| 3,368,982 | A | * | 2/1968 | Milbourne ............... 502/335 |
| 3,415,640 | A | * | 12/1968 | Lambert ............... 75/344 |

(Continued)

FOREIGN PATENT DOCUMENTS

WO    9955648    11/1999

(Continued)

OTHER PUBLICATIONS

Eurasian Patent Office Official Action Dated May 22, 2008; 1 page.

(Continued)

*Primary Examiner*—Cam N Nguyen
(74) *Attorney, Agent, or Firm*—Osha • Liang LLP

(57) ABSTRACT

More selective and efficient Ni hydrotreating catalysts are those which contain more than about 60% of the Ni content on the peripheral surface of porous supports, such as extruded alumina, which may be obtained by spraying an atomized solution of a Ni compound onto the support and drying it at a temperature in the range of from 200 to 600° C. When used, for example, to remove acetylenic compounds from butadiene streams, higher recovery of the desired butadiene with lower acetylenic content and low heavy polymer deposition is obtained than was possible with prior catalysts.

5 Claims, 6 Drawing Sheets

U.S. PATENT DOCUMENTS

| | | | |
|---|---|---|---|
| 3,793,388 | A | 2/1974 | Pitzer et al. |
| 4,179,408 | A | 12/1979 | Sanchez et al. |
| 4,273,735 | A | 6/1981 | Jacques et al. |
| 4,490,480 | A | 12/1984 | Lok et al. |
| 4,519,951 | A | 5/1985 | Qualeatti et al. |
| 4,734,392 | A | 3/1988 | Ganguli et al. |
| 4,780,447 | A | 10/1988 | Kim et al. |
| 5,028,665 | A | 7/1991 | Hucul |
| 5,036,037 | A | 7/1991 | Kladnig et al. |
| 5,223,472 | A | 6/1993 | Simpson et al. |
| 5,258,340 | A | 11/1993 | Augustine et al. |
| 5,446,003 | A * | 8/1995 | Augustine et al. ........... 502/159 |
| 5,756,420 | A | 5/1998 | Wittenbrink et al. |
| 5,866,734 | A | 2/1999 | Flick et al. |
| 5,958,825 | A | 9/1999 | Wulff-Doring et al. |
| 5,981,445 | A | 11/1999 | Kirchnerova et al. |
| 6,080,699 | A | 6/2000 | Pohl |
| 6,127,310 | A | 10/2000 | Brown et al. |
| 6,200,927 | B1 * | 3/2001 | Shukis et al. ............... 502/355 |
| 6,350,717 | B1 | 2/2002 | Frenzel et al. |
| 6,388,150 | B1 | 5/2002 | Overbeek et al. |
| 6,417,419 | B1 | 7/2002 | Abrevaya et al. |
| 6,437,206 | B1 | 8/2002 | Meyer et al. |
| 6,509,292 | B1 | 1/2003 | Blankenship et al. |
| 6,576,588 | B2 * | 6/2003 | Ryu et al. ................... 502/331 |
| 6,586,647 | B1 | 7/2003 | Abrevaya et al. |
| 6,780,817 | B1 | 8/2004 | Koyama et al. |
| 6,992,041 | B1 | 1/2006 | Yogo et al. |
| 7,022,645 | B2 * | 4/2006 | Ryu et al. ................... 502/328 |
| 7,030,052 | B2 | 4/2006 | Stochniol et al. |
| 7,056,488 | B2 * | 6/2006 | Niu et al. .................... 423/651 |
| 7,196,035 | B2 * | 3/2007 | Ryu et al. ................... 502/325 |
| 7,288,686 | B2 * | 10/2007 | Ryu ........................... 585/259 |
| 7,297,824 | B2 * | 11/2007 | Ryu et al. ................... 585/260 |
| 2002/0016519 | A1 | 2/2002 | Lok |
| 2002/0052289 | A1 | 5/2002 | Manzer et al. |
| 2003/0171629 | A1 * | 9/2003 | Ryu et al. ................... 585/260 |
| 2005/0032640 | A1 | 2/2005 | Huang et al. |
| 2005/0203320 | A1 * | 9/2005 | Ryu ........................... 585/261 |
| 2005/0209491 | A1 * | 9/2005 | Ryu ........................... 585/259 |

FOREIGN PATENT DOCUMENTS

WO          01/41922 A1    6/2001

OTHER PUBLICATIONS

Handbook of Commercial Catalysts, pp. 105-138, Howard F. Rase, CRC Press, 2000).
Eurasian Patent Office Official Action dated Oct. 15, 2008; 6 pages.
Supplemental Search Report issued by the European Patent Office dated Feb. 5, 2010.
U.S. Office Action issued in corresponding U.S. Appl. No. 11/950,920; dated Aug. 12, 2009; 9 pages.
First Office Action issued in the Chinese Patent application No. 200580001389.0 dated Mar. 6, 2009. (9 pgs.).
Office Action issued by USPTO dated Jan. 22, 2009 in U.S. Appl. No. 11/950,936 (19 pgs).

* cited by examiner

NI CATALYST, PROCESS FOR MAKING CATALYSTS AND SELECTIVE HYDROGENATION PROCESS

CROSS-REFERENCE TO RELATED APPLICATIONS

This application is a divisional application of U.S. patent application Ser. No. 10/828,823, filed Apr. 21, 2004, now U.S. Pat. No. 7,408,089, which claims the benefit of provisional application 60/554,627 filed Mar. 19, 2004, the disclosures of which are hereby incorporated by reference.

BACKGROUND OF THE INVENTION

1. Field of the Invention

The present invention relates to new selective hydrogenation catalysts and the method of making the catalysts, which are useful for hydrogenation, such as selective hydrogenation of acetylenic impurities in crude olefin and diolefin streams. In particular the invention relates to nickel-based catalysts.

2. Related Information

In the manufacture of olefins such as ethylene, propylene, butadiene, isoprene, etc., acetylenic impurities such as acetylene, methyl acetylene, vinyl acetylene, ethyl acetylene, 2-methyl-1-buten-3-yne, etc. in various crude mixed $C_2$-$C_5$ streams need to be removed with a minimum loss of useful materials such as ethylene, propylene, butenes, butadiene, isoprene, etc. in the feed streams.

1,3-butadiene is an important raw material used to produce various polymers such as butadiene-styrene copolymer. One of the processes for producing 1,3-butadiene is co-production of various olefins by steam cracking of petroleum fractions. The crude mixed $C_4$ stream from a steam cracker is selectively hydrogenated to partially remove $C_4$ acetylenic compounds. The selectively hydrogenated stream is sent to the 1,3-butadiene recovery unit where solvent extractive distillation techniques are used to separate 1,3-butadiene from the rest of components in the mixed stream. Solvent extractive distillation is expensive to operate and energy consumption is intensive.

Complete removal of $C_4$ acetylenic compounds in the stream with high recovery of 1,3-butadiene is highly desirable to reduce the production cost of 1,3-butadiene and produce a premium quality product for polymer production. However, formerly it was technically impossible to completely remove $C_4$ acetylenes in crude mixed streams by selective hydrogenation without unacceptably high loss of 1,3-butadiene due to over-hydrogenation of 1,3-butadiene. Therefore, an improved inexpensive process via a highly active and selective catalyst is highly desirable to produce premium quality 1,3-butadiene without paying a penalty for high loss of 1,3-butadiene due to over-hydrogenation.

The preferred technique for the purification in commercial practice is the selective hydrogenation of acetylenic compounds over hydrogenation catalysts. Supported Pd, Ni, Cu and Co catalysts are known as useful for the hydrogenation of acetylenes (Handbook of Commercial Catalysts, pp. 105-138, Howard F. Rase, CRC Press, 2000). The most preferred catalysts in prior commercial applications of selective hydrogenation of acetylenes are palladium-based catalysts such as Pd, Pd/Pb, Pd/Ag or Pd/Au on a support such as alumina and the copper catalysts on a support such as alumina. Pd catalysts were the most preferred catalysts because of high activity and supposedly superior selectivity compared with other metal catalysts.

Palladium-based catalysts are not selective enough to completely remove $C_4$ acetylenes without an unacceptable amount of 1,3-butadiene loss due to over-hydrogenation. Another inherent problem of palladium-based catalysts is the loss and migration of palladium due to the formation of soluble Pd complex compounds by the reaction of Pd atoms on the catalyst surface with vinyl acetylene, if the hydrogenation is carried out in the presence of liquid phase. Silver and gold have been used to minimize the loss of palladium and reduce catalytic polymerization of acetylenic compounds.

The copper-based catalysts are very selective so that the recovery of 1,3-butadiene from the mixed stream is very high compared with palladium-base catalysts. However, since the activity of copper catalysts is very low compared with palladium-based catalysts, a large volume of catalyst and large reactor are required. Also because of deposition of heavy carbonaceous materials on the catalyst is relatively fast, frequent regeneration of catalysts necessitates multiple reactors.

Ni catalysts in any form are very active catalysts for selective hydrogenation of acetylenes and dienes. According to R. S. Mann et al. (Can. J. Chem. 46, p. 623, 1968), Ni and Ni—Cu alloy catalysts are effective for methyl acetylene hydrogenation. The catalytic activity rapidly increases with addition of copper to nickel up to 25 wt. % in alloy catalyst. The selectivity to propylene and extent of polymerization increase with the increase of copper in the alloy. According to H. Gutmann and H. Lindlar (Organic Synthesis, Chapter 6), vinyl acetylene and 2-methyl-1-buten-3-yne are difficult to selectively hydrogenate to 1,3-butadiene and isoprene by using the usual palladium, nickel or cobalt catalysts.

Nickel-based catalysts have been used in commercial processes for the selective hydrogenation of acetylenic impurities in mixed steams of olefins and diolefins.

SUMMARY OF THE INVENTION

Briefly, the novel catalyst is an improvement in a selective hydrogenation catalyst comprising Ni deposited on a porous support wherein the improvement comprises having at least 60% of said Ni deposited on the periphery of the porous support, that is, on outer most skin of said porous support. The catalysts comprise Ni or Ni and one or more elements from Cu, Pd, Re, Zn, Mg, Mo or Bi. The catalysts are useful for hydrogenation reaction such as selective hydrogenation of acetylenic compounds in olefin or diolefin streams. Preferably nickel is the major active metal component; that is nickel will comprise over 50% by weight of the active meal components (Ni, Cu, Pd etc.) deposited on the porous support.

The active metal components are deposited on a porous support, such as transition alumina obtained by calcining at a temperature in a range between 750 and 1200° C. The preferred support will have an average pore diameter from about 100 Å to about 450 Å, BET surface area of greater than 10 $m^2/g$, preferably from about 20 $m^2/g$ to about 150 $m^2/g$, and total nitrogen adsorption pore volume from about 0.4 cc/g to about 1 cc/g. Preferably at least 60% of the Ni is deposited in the outer layer(s) of a shaped porous support. The preferred thickness of the outer skin layer of the catalyst is from about 0.03 mm to about 0.7 mm, preferably from about 0.04 mm to about 0.6 mm. The preferred amount of nickel deposited on the outer skin layer is from about 0.03 to about 3.5 $mg/m^2$, preferably from 0.05 to 2.5 $mg/m^2$. Depositing Ni on the catalyst is carried out either in one step or multi steps. The preferred technique depositing Ni in the outer layer of a support is spray-coating impregnation or optionally a combination of conventional impregnation such as incipient wet impregnation and spray-coating impregnation. The weight ratio of Pd to Ni on the catalyst is less than 0.05, preferably less than about 0.04.

The Pd modified Ni catalyst are particularly useful for removing MAPD. Methyl acetylene/propadiene (MAPD) is not a compound but covers the unstable compounds methyl acetylene and propadiene which may be depicted as follows: 1

DETAILED DESCRIPTION OF THE INVENTION

Catalysts

Figure 1:
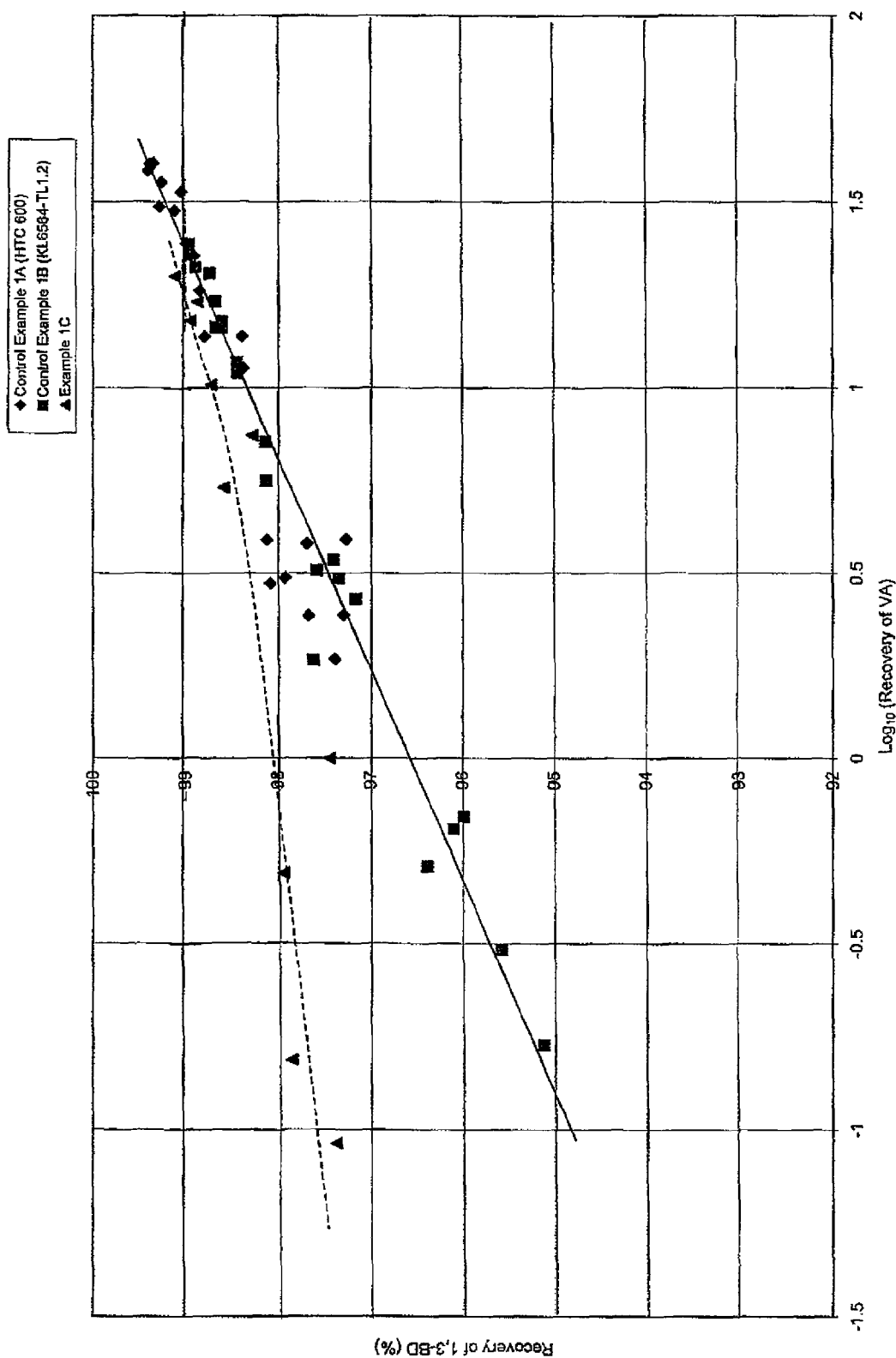
FIG. 1 is a chart comparing Control Examples 1A and 1B with Invention Example 1C for 1,3-butadiene recovery vs. vinyl acetylene recovery.

Preferably more than about 60% of the nickel component of the catalyst is deposited in the peripheral outer layer(s) of a shaped support in thickness of from about 0.03 mm to about 0.7 mm, preferably from 0.04 mm to about 0.6 mm, on a porous support. The preferred amount of nickel deposited on the outer skin layer is from about 0.03 to about 3.5 mg/m$^2$, preferably from 0.05 to 2.5 mg/M$^2$.

Examples of the preferred porous supports are alumina, silica, zirconia, talcite, silica-alumina, charcoal, or any inorganic support which has an average pore diameter from about 100 Å to about 450 Å, BET surface area from about 20 m$^2$/g to about 150 m$^2$/g, and total nitrogen adsorption pore volume from about 0.4 to about 1 cc/g. Alumina is the preferred support. The preferred alumina is transition alumina obtained by calcining at a temperature from about 750° to about 1200° C., preferably from about 800° to 1150° C. prior to use for the preparation of the catalysts. The preferred range of the total nickel content on the catalyst is from about 1 to about 20 weight %, preferably from 2 to 15 weight %.

The catalysts are useful for hydrogenation reactions such as selective hydrogenation to remove acetylenic impurities in various mixed streams of $C_2$-$C_{12}$ olefins, diolefins and styrene, and hydrogenation of benzene to cyclohexane. Passing a mixture of a hydrocarbon feed stream and hydrogen gas through a catalytic reaction zone or a series of two catalytic reaction zones carries out hydrogenation reactions such as the selective hydrogenation of acetylenic compounds. A catalytic reaction zone may contain one catalyst or several different catalysts. If the selective hydrogenation is carried out in a series of two catalytic reaction zones, optionally the catalyst in the second reaction zone may contain Cu as a promoter and modifier. The poisoning effects of organic mercaptans and organo-mercuric compounds for the nickel catalysts promoted with Cu in the second catalytic reaction zone are neutralized in the first catalytic reaction zone. A portion of the catalyst in the first catalytic reaction zone is sacrificed as a guard bed for the poisonous impurities. The improvement made for the hydrogenation process in this invention is higher selectivity or higher recovery of the useful materials such as mono-olefins, diolefins, or both, than those processes based on conventional nickel catalysts or conventional palladium-based catalysts. The $C_4$ acetylenic impurities in a mixed crude butadiene stream can be completely removed by selective hydrogenation with higher recovery of 1,3-butadiene in the present process, than prior art nickel catalysts. Therefore, this invention allows elimination of one of two extractive distillation columns, resulting in simpler and cheaper separation of 1,3-butadiene from the mixed stream.

The catalysts may be placed in any physical device to perform the selective hydrogenation of acetylenic compounds. The examples of such devices, in which chemical reactions related to this invention occur, are one or any combinations of fixed bed reactor, distillation column reactor, solvent extractive distillation column reactor, boiling point reactor, trickle bed reactor, moving bed reactor, fluidized reactor, stirred tank reactor, divided wall reactors, divided wall distillation column reactors, etc.

The catalysts may comprise Ni only on a support or Ni and one or more elements from Cu, Pd, Re, Zn, Mg, Mo or Bi to improve the catalyst activity, stability, and the recovery of olefins and diolefins from the crude mixed streams. The major roles of CU, Pd and Re are promoters for higher catalyst activity as well as modifiers to improve the recovery of olefin and diene products. The active metal components are deposited on a porous support such as alumina, silica, basic silica-alumina, carbon, charcoal, etc. Alkali or alkaline earth metals may be incorporated into alumina supports prior to deposition of Ni.

The preferred support will have the following properties. The preferred shaped support will have the size from about 0.2 to 7 mm. The preferred support will have an average pore diameter from about 100 to about 450 Å, more preferably about 140 to about 400 Å, BET surface area from about 20 to about 150 m$^2$/g, and total nitrogen adsorption pore volume from about 0.4 to 1 cc/g. Alumina is one of the preferred supports. The preferred alumina in this invention will have at least 30%, preferably at least 50% of the pores larger than 100 Å diameter, and a total pore volume from about 0.45 cc/g to 1 cc/g and ABD (apparent bulk density) from about 0.35 to about 0.75 g/cc.

Ni catalyst modified with one or more elements among Cu, Pd, Zn, Mg, Mo or Bi may be prepared by incorporating the appropriate amount of these modifying components into the alumina during its manufacture, preferably as compounds.

The preferred alumina disclosed in this invention can be prepared by a number of techniques well known to those skilled in the art. One of the preferred aluminas disclosed in this invention can be prepared by so-called oil dropping gelation technique as disclosed in U.S. Pat. No. 2,620,314 (1952), and U.S. Pat. No. 4,273,735 (1981). The spherically shaped alumina is prepared from aluminum hydroxychloride sol prepared by digesting aluminum metal in aqueous hydrochloric acid solution. Spherically shaped alumina sol materials, in the form of droplets, are gelled in basic liquid oil phase followed by aging, washing, drying, and calcining to obtain usually gamma-alumina in commercial production at an elevated temperature. Alternatively the preferred spherically shaped alumina also can be prepared by oil dropping gelation technique using the dispersed boehmite or pseudoboehmite alumina sols as disclosed in U.S. Pat. No. 4,179,408 (1979). The alumina sols are prepared by dispersing suitable boehmite, pseudoboehmite or mixtures of boehmite and pseudoboehmite aluminas in acidic water. The pseudoboehmite or boehmite raw materials are prepared by hydrolyzing aluminum alkoxides and crystallizing or reacting sodium aluminate with aluminum salts such as aluminum sulfate and crystallizing. Various boehmite aluminas or dispersed boehmite aluminas sols are available in the marketplace. Condea is one of the suppliers. To prepare the preferred spherical alumina whose pore structure is disclosed herein, Disperal HP 14/2, Dispal 11N7-80, Dispal 23N4-20, Disperal HP 14, Deperal 40, Pural 200, Pural 100, Pural NG, etc. or mixtures of these can be used. The preferred alumina is transition alumina calcined at in a temperature range from about 750° to about 1200° C., comprising gamma, delta, kappa, theta and alpha crystalline forms or mixtures thereof.

The preferred alumina in various extrudate forms can also prepared by extruding the preferred boehmite or pseudoboehmite aluminas discussed above, and calcining at elevated temperatures from about 750° C. to 1200° C. The modifiers disclosed herein (Cu, Re, Zn, Mg, Mo, and Bi or others known in the art) may at least in part be incorporated into the alumina prior to extrusion. The surface area of alumina tends to shrink by repeated exposures to elevated temperatures due to slow crystallization to more stable crystal forms. This surface area shrinkage accelerates in the presence of atmospheric moisture or trace amount of sodium in the alumina or both. Usually alumina support for the catalyst preparation is commercially produced as gamma alumina by the calcination at temperatures from about 550° C. to 700° C. The physical shapes of the preferred aluminas can be any shape such as spheres, extrudates, pellets and granules which have diameter of less than about ¼ inches, preferably ⅛ inches and less than about ½ inches length, preferably less than ¼ inches length for extrudates or pellets.

Preferably 60% or more nickel metal on the catalysts is deposited in the outer peripheral region of the shaped porous support, rather than within the support. The preferred thickness of the outer skin layer of the Ni catalysts is from about 0.03 mm to about 0.7 mm, more preferably from 0.04 mm to 0.6 mm, most preferably from 0.04 mm to 0.50 mm. No prior at or publication is known to disclose the use of a material for the hydrogenation reaction, where nickel metal is preferably deposited in the outer layer region of a shaped porous support. Total nickel content of the catalyst is preferably from about 3 to 20 wt. %, more preferably from 4 to 15 wt, %. To obtain a predetermined metal composition on a catalyst within a desired thickness of layer, one may carry out either one or multiple impregnations of properly prepared solutions of a nickel compound or mixed solutions of nickel and modifier compounds on a support. The preferred technique depositing nickel metal in the outer layer is spray-coating impregnation of a suitable solution of nickel compound on a support. When multiple spray coating impregnation is carried out, the product from an impregnation step is preferably either dried or calcined at a temperature in the range from 200 to 800° C., preferably 250 to 500° C., prior to carrying out the next impregnation. The catalysts can be prepared either in one step or multi steps. The nickel or nickel and other components of a catalyst may be deposited by spray coating a solution of nickel compound or a mixed solution of nickel and the modifier compounds on a support. Optionally one may deposit nickel and copper components separately by carrying out a series of two or more impregnations.

If palladium is also deposited in the outer peripheral region with Ni, the amount of Pd on the catalyst is from up to 1 wt. %, preferably from 0.005 to 0.25 wt. % of the total catalyst. The deposition of Pd on the catalyst can be carried out simultaneously with Ni deposition by using a mixed solution of Ni compound and Pd compound or the Pd can be deposited in a separate step in any order, but preferably Pd is deposited after the Ni. Preferably 100% of the Pd on the catalyst is deposited in the outer peripheral region of the shaped porous support, rather than within the support.

In an alternative multiple impregnation technique, the deposition of nickel metal on a support is carried out in a combination of conventional impregnation and spray-coating impregnation in series. For example, the conventional impregnation such as incipient wet impregnation is carried out in the first impregnation and then spray-coating impregnation is performed in the second step. The product from the incipient wet impregnation is preferably subjected to a thermal treatment from about 200° to 800° C., more preferably from about 250° to about 500° C., prior to spray-coating impregnation. Optionally one may carry out the spray-coating impregnation in the first step and the conventional impregnation in the second step.

When a copper containing Ni catalyst is prepared with an alumina support, the content of copper on the catalyst is in a range of from about 0.005 to about 10 wt. %. The solution of the nickel compound is prepared by dissolving a nickel compound in water or an organo nickel compound in organic solvent or water. Molten liquid of a nickel compound such as nickel nitrate hexahydrate can be used for the spray coating impregnation instead of aqueous nickel nitrate solution. The examples of the nickel compounds are nickel salts such as nickel nitrate or organo metallic nickel compounds such as nickel acetate, nickel formate, nickel acetylacetonate, nickel alkoxides, etc. After the completion of spraying a solution on a support, the impregnation product is preferably subjected to a thermal treatment at a temperature from about 200 to about 800° C., more preferably from about 250 to about 500° C., from 10 minutes to 24 hours. The preferred volume of the liquid for spray coating impregnation is from about 2 to 70 volume %, preferably 2 to about 25 volume % of the total pore volume of a support. Fine liquid droplets of impregnation solution of a nickel compound to perform spray-coating impregnation on a support may be produced by using either liquid sprayer or atomizer. The spray-coating is carried out at either ambient or elevated temperature. The elevated temperature spray-coating is carried out on a porous support presented to a temperature from about 100 to 350° C. Preferably fine liquid droplets are sprayed on shaped supports rolling in a rotary impregnator or on a flat surface.

Hydrogenation Process

The feed containing acetylenic compounds and other unsaturated compounds is passed through catalytic reaction zone(s) in gas phase, liquid phase or a mixed phase of gas and liquid. The temperature of the selective hydrogenation reaction in the catalytic reaction zone is one of the most important process variables. The temperature is in a range of about 50° F. to about 420° F., preferably from about 55° F. to about 380° F. However, the temperature is determined by the specific acetylenic compounds to be hydrogenated and the physical phase of the hydrocarbons in a specific catalytic reaction zone. For the $C_2$ or $C_3$ acetylene in a mixed $C_2$ or $C_3$ olefinic hydrocarbon feed, the temperature for the selective hydrogenation is in a range of from about 55° F. to 380° F. For the $C_4$ acetylenic compounds in a mixed butadiene stream, the temperature is in a range of from about 50° F. to 200° F., preferably from 55° to 180° F. For the $C_5$ acetylenic compounds in a mixed $C_5$ diolefinic hydrocarbons stream, the temperature is in a range of from about 60° F. to about 250° F. For heavier acetylenic hydrocarbons than C5 acetylenes in heavier hydrocarbons than $C_5$, the temperature is in a range of from about 65° F. to about 350° F.

The concentration of hydrogen in the catalytic reaction zones is another critically important process variable. The concentration of hydrogen in the catalytic reaction zone depends on a number of factors; the concentration of acetylenic compounds in the incoming feed stream into a specific reaction zone, the specific acetylene compounds(s), the intended conversion of acetylenes across a specific catalytic reaction zone, the hydrocarbon phase of the catalytic reaction zone whether single phase or mixed phase, the temperature of a specific catalytic reaction zone, catalyst composition in a specific reaction zone, and the specific physical device of the catalytic reaction zone, such as a fixed bed reactor or catalytic distillation column reactor. In general, the minimum amount of hydrogen is no less than 50 mole %, preferably 70 mole %, of the concentration of the total acetylenes in the incoming stream into a specific catalytic reaction zone. The maximum amount of hydrogen in the catalytic reaction zone in fixed bed operation is no higher than 5 times, preferably no higher than 3 times, of the moles of total acetylenic compounds. In general, more hydrogen is needed for the catalytic distillation or catalytic extractive distillation operation than the fixed bed operation.

The pressure of a catalytic reaction zone is determined by the following specifics: the specific physical device of a catalytic reaction zone, whether a solvent is used or not, the intended temperature of a selective hydrogenation reaction in a specific catalytic reaction zone, and the intended phase (gas, liquid or a mixed phase of gas and liquid) of hydrocarbons in the catalytic reaction zone.

The flow rate of the hydrocarbons in a specific reaction zone is determined by the following: catalyst composition, the specific physical device of a catalytic reaction zone, intended conversion of acetylenic compounds across the specific catalytic reaction zone, and the concentration of hydrogen, temperature and pressure in a specific catalytic reaction zone.

The evaluation of the catalysts performance is carried out by comparing recovery of a desired product for a given feed stock at a given conversion of acetylenic compounds or at the conversion required to meet specific product qualification against the prior art. For example, when $C_4$ acetylenic compounds in a crude butadiene stream are selectively hydrogenated, 1,3-butadiene is the desired product to be recovered from the feed stream, the following mathematical formula defines the recovery of 1,3-BD.

$$\text{Recovery of } 1,3\text{-}BD(\%) = 100 - (N_F - N_P) \times 100/N_F$$

where: $N_F$=wt. % of 1,3-BD in feed stream, and $N_P$=wt. % of 1,3-BD in product stream The recovery of vinyl acetylene (VA) or ethyl acetylene (EA) is defined in an identical manner. Since vinyl acetylene can be converted to 1,3-BD by hydrogenation, the recovery of 1,3-BD is mathematically possible to be larger than 100%. This is also true for the selective hydrogenation of methyl acetylene (MA) in a crude $C_3$ cut stream. The recovery of propylene from a crude $C_3$ cut stream can be larger than 100%, because MAPD can be converted to propylene by selective hydrogenation.

The complete or near complete conversion (to less than 30 ppm total combined $C_4$ acetylene) of $C_4$ acetylenes with high recovery of 1,3-butadiene leads to elimination of one of two extractive distillation units to separate 1,3-butadiene from the mixed stream. The result is a cheaper production cost of 1,3-butadiene.

When the selective hydrogenation is carried out in a series of two catalytic reaction zones for a better recovery of 1,3-BD, the concentration of combined acetylenic impurities in the product stream from the first catalytic reaction zone is in a range from about 100 wt. ppm to about 5000 wt. ppm, depending on the concentration of acetylenic impurities in the feed stream. The recovery of 1,3-butadiene across the first catalytic reaction zone is preferably maintained at higher than about 96 wt. %. The first catalytic reaction zone also serves to maximize the isomerization of propadiene to methyl acetylene and 1,2-butadiene to 1,3-butadiene. However, it is possible to completely remove all the acetylenic impurities in the feed stream by passing through a single catalytic reaction zone.

The product stream from the first catalytic reaction zone is passed through the second catalytic reaction zone with or without an adjustment of hydrogen at optimal process conditions. In the product stream from the second catalytic reaction zone, the concentration of the combined $C_4$ acetylenic impurities is in a range from 0 wppm to about 30 wppm. The recovery of 1,3-butadiene across the second catalytic reaction zone is better than about 97 wt. %.

A Ni catalyst or two different Ni catalysts may be loaded in a single reactor in any physical device for any operational mode. Optionally two separate reactors serve as two catalytic reaction zones where two different catalysts are loaded. The selective hydrogenation of acetylenic impurities can be carried out in various configurations for the reaction zone. Carrying out the reaction in any combination of modes such as fixed bed reactor, catalytic distillation reactor, solvent extractive catalytic distillation reactor, boiling point reactor, moving bed reactor, fluidized reactor, divided wall reactor, etc. is part of this invention. Such examples are two serial fixed beds, a catalytic distillation column reactor for the first catalytic reaction zone and a second fixed bed reactor for the second catalytic reaction zone, a fixed bed reactor for the first reaction zone with a solvent extractive catalytic distillation column reactor for the second reaction zone, etc.

The performance of a catalyst deteriorates with on-stream time due to various reasons. One of the reasons is slow build-up of poisonous carbonaceous materials on the catalyst surface. To prolong the catalyst cycle or service time, a solvent may be used to wash off heavy polymers to slow the build-up rate of the poisonous carbonaceous materials on the catalyst. Therefore, heavy polymers should be soluble, at least to some degree, in the solvent under the selective hydrogenation conditions. Examples of such solvents include cyclohexane, methyl cyclohexane, benzene, toluene, alkyl nitrites, furfural, dimethyl acetamide, dimethyl formamide, methylpyrrolidone, formylmorpholine, and ethers such as tetrahydrofuran. The solvent is recovered from the reactor effluent stream to recycle. Optionally the solvent may be build up in the system, at the start-up of the unit, by recycling heavy components, which is usually a small part of the feed and is also produced by oligomerization and polymerization during the selective hydrogenation in the catalytic reaction zone(s). Solvent is co-fed with feed to the catalytic reaction zone for the fixed bed operation. For the catalytic distillation or extractive catalytic distillation operation, solvent is introduced at a position in the top half of the column. Another alternative operational procedure is occasional washing the catalysts with solvent at a temperature in a range of from 70° F. to 750° F. under a pressure from 0 to 500 psi, preferably in the presence of hydrogen. Deposition of heavy polymer on selective hydrogenation catalysts can deactivate the catalyst and require regeneration. It has been found that the present Ni catalysts exhibit very low polymer deposition compared to commercially available catalysts.

CONTROL EXAMPLE 1A

Conventional Catalyst

Figure 2:
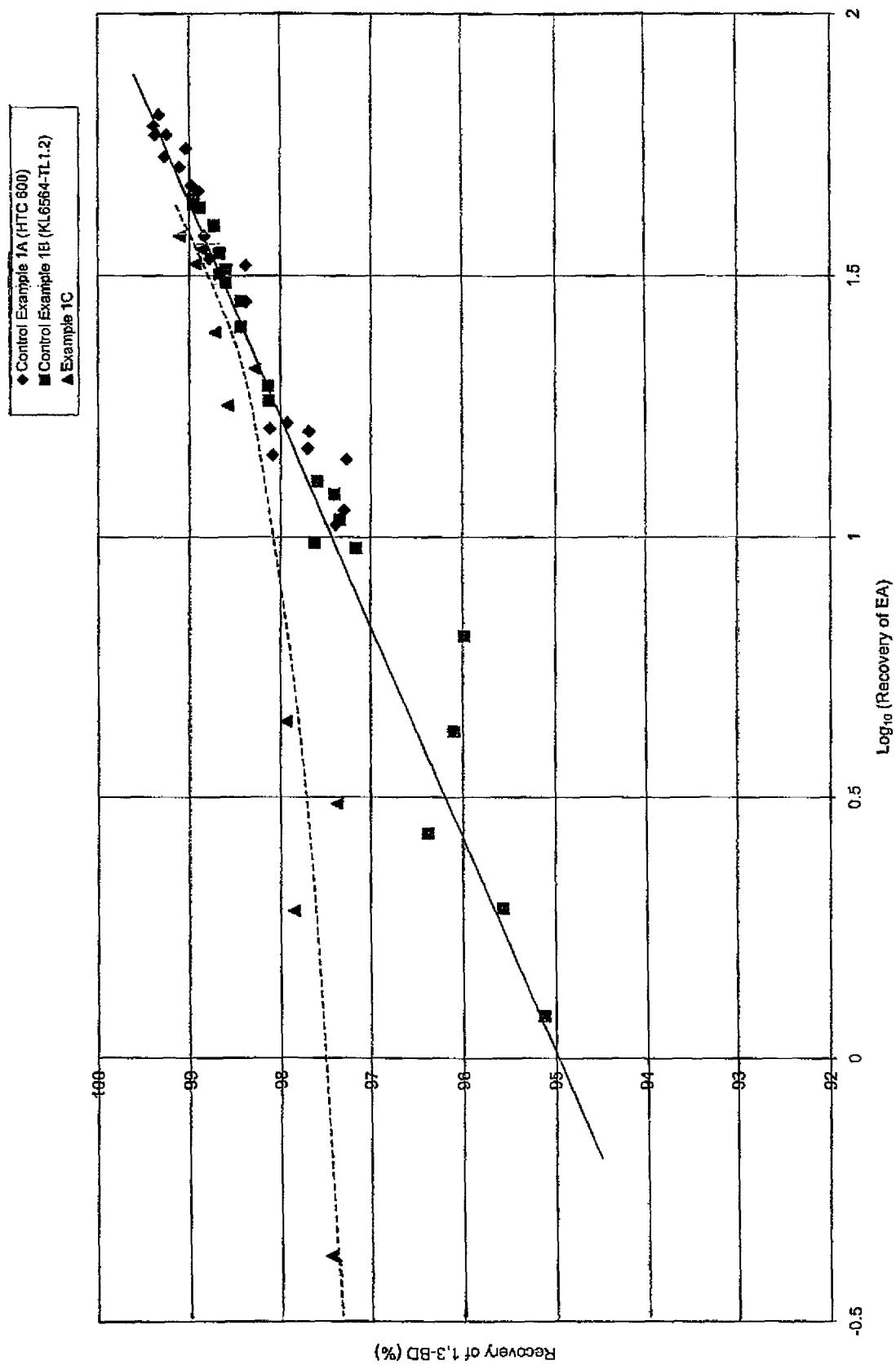
FIG. 2 is a chart comparing Control Examples 1A and 1B with Invention Example 1C for 1,3-butadiene recovery vs. ethyl acetylene recovery.

Commercial 28 wt. % Ni catalyst (HTC 600-RP1.2 obtained from Synetix) was tested to remove $C_4$ acetylenic impurities in a crude steam cracked butadiene stream by selective hydrogenation. 50 grams of the catalyst were mixed with 70 ml of 3 mm diameter glass balls and loaded in a vertically mounted up-flow stainless fixed bed reactor (1 inch diameter×20 inch long). The catalyst is 1.2 mm diameter trilobe extrudate. Two thermocouples at each end of catalyst zone were installed to control the reactor temperature. The catalyst was supplied by the manufacturer as activated and passivated form, and recommended reactivating at 482° F. in hydrogen gas flow. The catalyst was reactivated at 250° F. in 300 cc/min gas flow of 33 volume % hydrogen gas in nitrogen for 1.5 hours and then 575° F. for 5 hours by passing 350 cc per min of pure hydrogen gas. The reactor was cooled to ambient temperature. The selective hydrogenation of acetylenic impurities in a crude steam cracked butadiene feed was carried out at 6 ml/min of hydrocarbon feed and at 80 sccm/min of hydrogen flow rate at the beginning of the reaction, down to 55 sccm/min toward to the end of the run, and under 108 psig total reactor pressure. The feed was comprised of 1.071 wt. % vinyl acetylene, 0.16 wt % ethyl acetylene and 0.22 wt % methyl acetylene, 71.33 wt % 1,3-BD, 0.18 wt % 1,2-BD, 15.03 wt % butenes, etc. Because of the exothermic heat of hydrogenation, the temperature at the end of the catalyst bed was higher than at the beginning of the catalyst bed. The temperature of the hydrogenation was 118° to 124° F. at the end of the catalyst bed and 88° to 99° F. at the beginning of the catalyst bed, respectively. The best quality product from this experiment contained 190 ppm VA and 150 ppm EA at 97.4% recovery of 1,3-butadiene. The result is illustrated in FIGS. 1 and 2.

CONTROL EXAMPLE 1B

Conventional Catalyst

Commercial 28% wt % Ni catalyst (KL6564-TL1.2 obtained from CRI) was tested to remove $C_4$ acetylenic impurities in a crude steam cracked butadiene stream by selective hydrogenation. The catalyst is 1.2 mm diameter trilobe extrudate. The catalyst has 113 m²/g BET surface, 0.43 cm³/g total $N_2$ adsorption pore volume and 12.8 nm average pore diameter. 50 grams of the catalyst were mixed with 60 ml of 3 mm diameter glass balls and loaded in a vertically mounted up-flow stainless fixed bed reactor (1 inch diameter×20 inch long). Two thermocouples at each end of catalyst zone were installed to control the reactor temperature. The catalyst was supplied by the manufacturer as activated and passivated form, and recommended reactivating at 450° F. in hydrogen gas flow. The catalyst was reactivated at 250° F. in 300 cc/min gas flow of 33 volume % hydrogen gas in nitrogen for 1.5 hours and then 575° F. for 5 hours by passing 350 cc per min of pure hydrogen gas. The reactor was cooled to ambient temperature. The selective hydrogenation of acetylenic impurities in the same feed used in the Control Example 1A was carried out at 6 ml/min of hydrocarbon feed and at 80 sccm/min of hydrogen flow rate at the beginning of the reaction down to 50 sccm/min toward to the end of the run under 108 psig total reactor pressure. The temperature of the hydrogenation was 1180 to 125° F. at the end of the catalyst bed and 76° to 90° F. at the beginning of the catalyst bed, respectively. The best quality product from this experiment contained 18 ppm VA and 19 ppm EA at 95.1% recovery of 1,3-butadiene. The result is illustrated in FIGS. 1 and 2.

EXAMPLE 1C

Invention

The catalyst was prepared by carrying out two spray-coating impregnations at ambient temperature. The gamma-alumina used to prepare the nickel catalyst is 1.68 mm diameter spheres prepared by the oil dropping gelation technique. The physical properties of the alumina as received from the manufacturer are summarized in Table 1. More than about 90% of the pores in this alumina have a diameter larger than 100 Å. The average pore diameter is 214 Å. The alumina is unsuitable to use for the preparation of the catalyst as it is, according to the present invention. Therefore, the alumina was calcined at 1100° C. for 3 hours in air to prepare a suitable alumina for the catalyst preparation. After calcination, the average diameter of alumina spheres shrunk to 1.45 mm from 1.68 mm. The average pore diameter was 362 Å. The physical properties of this calcined alumina are listed in Table 2. The XRD of this calcined alumina indicates theta alumina with some delta. Nickel metal was deposited on this calcined alumina as a peripheral layer of about 0.38 mm thickness by carrying out multiple impregnations with nickel nitrate solution as described below.

TABLE 1

| | |
|---|---|
| ABD, g/cc | 0.48 |
| BET, m²/g | 170.2 |
| Micro Pore Area, m²/g | 0 |
| Total pore volume (cc/g) for pores less Than 493 Å radius at $P/P_0 = 0.9801$ | 0.912 |
| Average Pore diameter, Å | 214.4 |

TABLE 2

| | |
|---|---|
| ABD, g/cc | 0.62 |
| BET, m²/g | 67.4 |
| Micro Pore Area, m²/g | 3.0 |
| Total pore volume (cc/g) for pores less Than 493 Å radius at $P/P_0 = 0.9801$ | 0.701 |
| Average Pore diameter, Å | 362 |

A nickel nitrate solution was prepared by dissolving 70 g $NiNO_3.6H_2O$ in 36 grams of water for the first impregnation. 300 grams of the calcined alumina were placed in a rotary impregnator and then the above nickel nitrate solution was sprayed on the rolling alumina spheres with an atomizer at ambient temperature over a period of about 10 minutes. After drying the impregnation product at about 200° C. by blowing hot air into the rotary impregnator, the dried product was calcined at 350° C. for about 2 hours. Another nickel solution was prepared for the second impregnation by dissolving 60 grams of $NiNO_3.6H_2O$ in 31.5 grams of water. The second impregnation was carried out on the calcined, first impregnation product in similar manner to the first impregnation. After drying at 200° C., the calcination at 420° C. was carried out for 2 hours. The amount of nickel deposited on the alumina support is 8.05 wt. % based on the total amount of nickel nitrate used. The catalyst had the following physical properties; 70.3 m²/g BET surface area, 0.590 cm³/g of total nitrogen pore volume and 317 Å of average pore diameter. The examination of the calcined product under a microscope indicates about 0.38 mm of the thickness of the peripheral nickel oxide layer on the alumina spheres which means about 0.78 mg Ni metal loading per $m^2$ in the layer.

80 g of this catalyst were loaded in the same reactor used in the Control Example 1. The catalyst was activated at 250° F. in 300 cc/min gas flow of 33 volume % hydrogen gas in nitrogen for 1.5 hours, 670° F. for 3 hours and then 750° F. for 3 hours by passing 350 cc per min of pure hydrogen gas. The reactor was cooled to ambient temperature. The selective hydrogenation of acetylenic impurities in the same feed used in the Control Example 1A was carried out at 6 ml/min of hydrocarbon feed and at 65 sccm/min of hydrogen flow rate at the beginning of the reaction down to 55 sccm/min toward to the end of the run under 108 psig total reactor pressure. The temperature at the end of the catalyst bed was higher than at the beginning of the catalyst bed. The temperature of the hydrogenation was 1200 to 130° F. at the end of the catalyst bed and about 74° F. at the beginning of the catalyst bed, respectively. The best quality product from this experiment contained 0 ppm VA and 6 ppm EA at 97.5% recovery of 1,3-butadiene. The present nickel catalyst demonstrates a superior catalytic performance to those of the Control Examples 1A and 1B.

CONTROL EXAMPLE 2A

Conventional Catalyst

Figure 3:
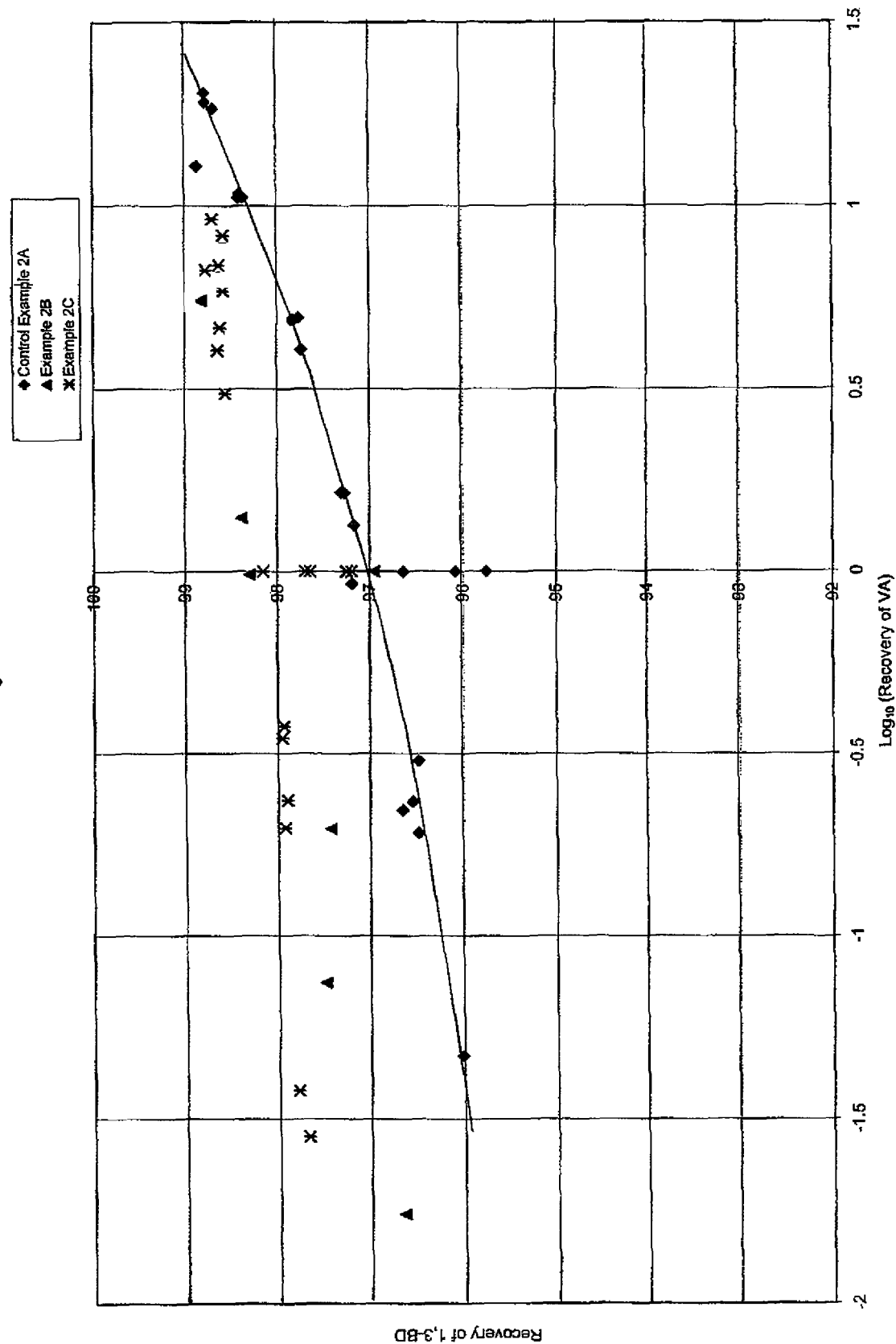
FIG. 3 is a chart comparing Control Example 2A with Invention Examples 2B and 2C for 1,3-butadiene recovery vs. vinyl acetylene recovery.
Figure 4:
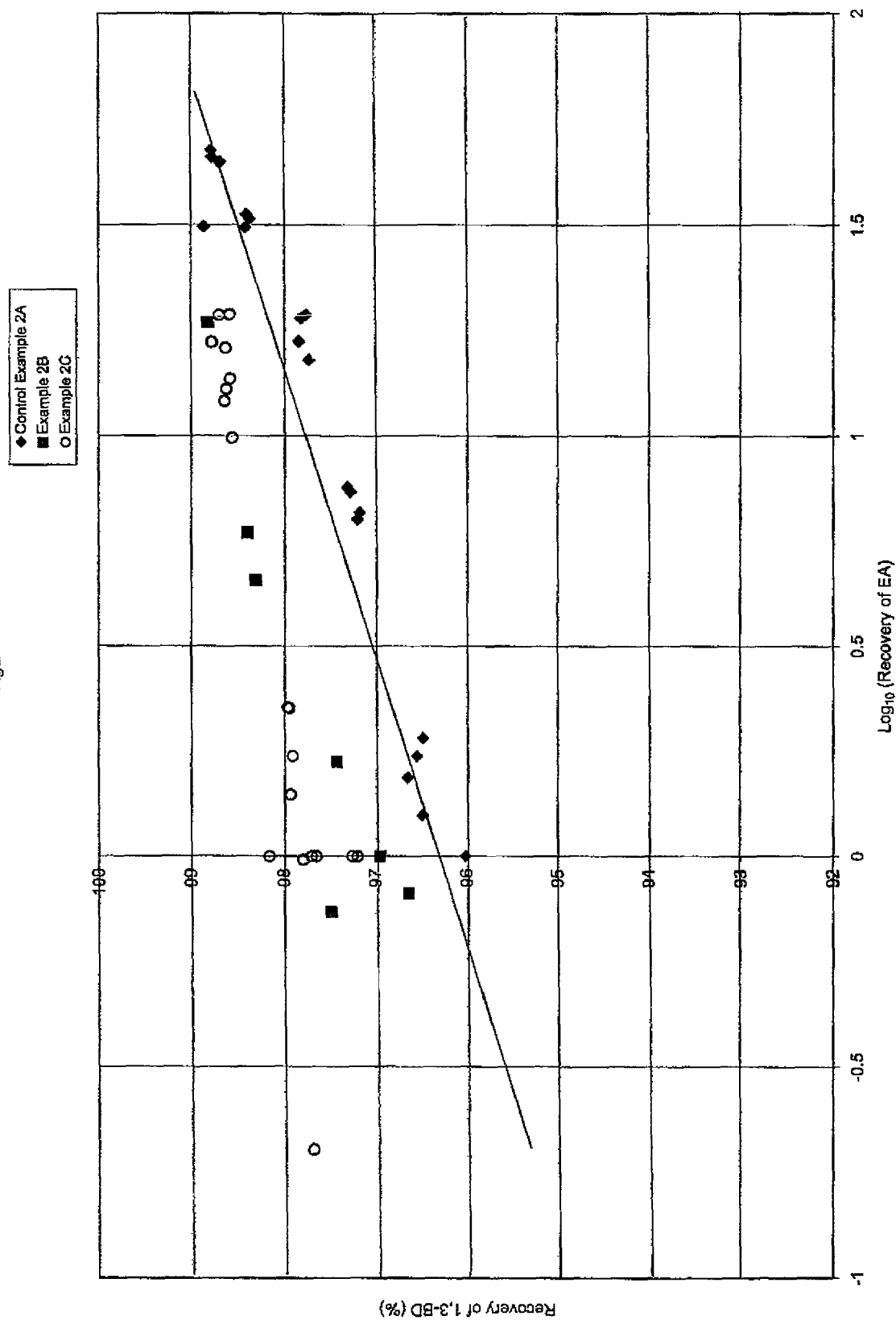
FIG. 4 is a chart comparing Control Example 2A with Invention Examples 2B and 2C for 1,3-butadiene recovery vs. ethyl acetylene recovery.

Commercial 28% wt % Ni catalyst (KL6564-TL1.2 obtained from CRI) was tested to remove $C_4$ acetylenic impurities in a crude steam cracked butadiene stream by selective hydrogenation. 50 grams of the catalyst were mixed with 60 ml of 3 mm diameter glass balls and loaded in a vertically mounted up-flow stainless fixed bed reactor (1 inch diameter×20 inch long). Two thermocouples at each end of the catalyst zone were installed to control the reactor temperature. The catalyst was supplied by the manufacturer as activated and passivated form, and recommended reactivating at 450° F. in hydrogen gas flow. The catalyst was reactivated at 250° F. in 300 cc/min gas flow of 33 volume % hydrogen gas in nitrogen for 1.5 hours and then at 670° F. for 5 hours by passing 350 cc per min of pure hydrogen gas. The reactor was cooled to ambient temperature. The selective hydrogenation of acetylenic impurities in a crude steam cracked butadiene feed was carried out at 6 ml/min of hydrocarbon feed and at 65 sccm/min of hydrogen flow rate at the beginning of the reaction down to 40 sccm/min toward to the end of the run under 108 psig total reactor pressure. The feed was comprised of 0.98 wt % vinyl acetylene, 0.12 wt. % ethyl acetylene and 0.08 wt. % methyl acetylene, 72.52 wt. % 1,3-BD, 0.01 wt. % 1,2-BD, 14.05 wt. % butenes, etc. The temperature of the hydrogenation was 120° to 124° F. at the end of the catalyst bed and 900 to 99° F. at the beginning of the catalyst bed, respectively. The best quality product from this experiment contained 5 ppm VA and 0 ppm EA at 95.9% recovery of 1,3-butadiene. The result is illustrated in FIGS. 3 and 4.

EXAMPLE 2B

Invention

The following demonstrates superior performance of the catalyst of the present invention to that of the Control Example 2A. The catalyst was prepared by carrying out two spray-coating impregnations of nickel nitrate solutions on hot alumina supports. The same alumina calcined at 110° C. for 3 hours used in the Example 1C was used to prepare the nickel catalyst in this example.

A nickel nitrate solution was prepared by dissolving 86.5 g $NiNO_3.6H_2O$ in 48 grams of water for the first impregnation. 300 grams of the calcined alumina were preheated to about 205° C. in an oven and then the hot alumina was placed in a rotary impregnator for impregnation with the nickel nitrate solution over a period of about 20 minutes using an atomizer. During the spray coating impregnation, the rotary impregnator was heated with hot air. The impregnation product was dried at about 200° C. by blowing hot air into the rotary impregnator. The dried product was calcined at 420° C. for 3 hours. Another nickel nitrate solution of the same concentration was prepared for the second impregnation. The second impregnation was carried out on the calcined first impregnation product preheated to about 205° C. in the similar manner to the first impregnation. After drying at 200° C., the calcination was carried out at 450° C. for 3 hours. The net amount of nickel deposited on the alumina support was 10.4 wt. % based on the total amount of nickel nitrate used. The dried product under the microscope indicates 0.32 mm of the layer thickness, which means about 2.09 $mg/m^2$ Ni metal loading in the layer.

60 g of this catalyst were loaded in a vertically mounted up-flow stainless fixed bed reactor (1 inch diameter×20 inch long). The catalyst was activated at 250° F. in 300 cc/min gas flow of 33 volume % hydrogen gas in nitrogen for 1.5 hours and then for 3 hours at 670° F. and 3 hours at 770° F. by passing 350 cc per min of pure hydrogen gas. The reactor was cooled to ambient temperature. The selective hydrogenation of acetylenic impurities in the same feed used in the Control Example 2A was carried out at 6 ml/min of hydrocarbon feed and at 55 sccm/min of hydrogen flow rate at the beginning of the reaction, down to 45 sccm/min toward to the end of the run, under 108 psig total reactor pressure. The temperature of the hydrogenation was 118° to 123° F. at the end of the catalyst bed and about 80° F. at the beginning of the catalyst bed, respectively. The best quality product from this experiment contained 0 ppm VA and 0 ppm EA at 97.4% recovery of 1,3-butadiene. The result is illustrated in FIGS. 3 and 4 to show a superior performance of this example to those of the Control Example 2A.

EXAMPLE 2C

Invention

The catalyst in this example was prepared by carrying out two spray-coating impregnations of nickel nitrate solutions at ambient temperature.

A nickel nitrate solution was prepared by dissolving 86.5 g $NiNO_3.6H_2O$ in 25.95 grams of water for the first impregnation. 300 grams of the same calcined alumina used in the Example 1C were placed in a rotary impregnator and the impregnation was carried out by spraying the nickel nitrate solution on the alumina spheres rolling inside the rotary impregnator with an atomizer over a period of about 10 minutes. After drying the impregnation product at about 200° C. by blowing hot air into the rotary impregnator. The dried product was calcined at 350° C. for about 3 hours. Another nickel solution was prepared for the second impregnation by dissolving 47.3 grams of $NiNO_3.6H_2O$ in 14.19 grams of water. The second impregnation was carried out on the calcined first impregnation product in the similar manner to the first impregnation. After drying at 200° C., the dried impregnation product was calcined at 350° C. for 2 hours. The amount of nickel deposited on the alumina support was 8.26 wt. % based on the total amount of nickel nitrate hexahydrate used. The finished catalyst had the following physical properties; 64.7 m²/g BET surface area, 311 Å average pore diameter, and 0.694 cm³/g total nitrogen pore volume.

The observation of the finished catalyst spheres under a microscope indicates that there are three regions in each catalyst sphere: an outer layer, inner layer and a core center region. The average thickness of the outer two layers is about 0.32 mm (1.45 mm of alumina sphere diameter). Therefore, the total nickel metal loading in the layers is about 1.61 mg/m² on average. The outermost layer has a thickness of from about 0.125 to about 0.145 mm. The outer layer was created by the second spray-coating impregnation. No nickel deposition in the white core center region is observed. Therefore, the nickel loading in both the outer most layer and the inner layer in the first impregnation is about 1.04 mg/m². But the second impregnation deposited 0.70 mg/m² in the outer layer, resulting in about 1.74 mg of the net Ni deposit per m². Therefore, 88 wt. % of total Ni on the catalyst was loaded in the outermost layer and 12 wt. % was loaded in the inner layer.

60 g of this catalyst were loaded in a vertically mounted up-flow stainless fixed bed reactor (1 inch diameter×20 inch long). The catalyst was activated at 250° F. in 300 cc/min gas flow of 33 volume % hydrogen gas in nitrogen for 1.5 hours, and then for 3 hours at 670° F. and for 3 hours at 770° F. by passing 350 cc per min of pure hydrogen gas. The reactor was cooled to ambient temperature. The selective hydrogenation of acetylenic impurities in a crude steam cracked butadiene feed was carried out at 6 ml/min of hydrocarbon feed and at 52 sccm/min of hydrogen flow rate at the beginning of the reaction, down to 44 sccm/min toward to the end of the run, under 108 psig total reactor pressure. The feed was comprised of 1.06 wt % vinyl acetylene, 0.15 wt. % ethyl acetylene and 0.16 wt. % methyl acetylene, 71.34 wt. % 1,3-BD, 0.19 wt % 1,2-BD, 14.59 wt. % butenes, etc. The temperature of the hydrogenation was 119 to 122° F. at the end of the catalyst bed and 760 to 83° F. at the beginning of the catalyst bed, respectively. The best quality product from this experiment contained 0 ppm VA and 0 ppm EA at 97.7% recovery of 1,3-butadiene. The result is illustrated in FIGS. 3 and 4 to show a superior performance of this example to those of the Control Example 2A.

CONTROL EXAMPLE 3A

Four different commercial nickel catalysts were tested in this experiment.

The catalysts were HTC-600 (28% Ni), HTC-500 (20% Ni), KL6564 (28% Ni) and KL6560 (18% Ni). These catalysts are all trilobe extrudates of 1.2 mm diameter. The catalysts were supplied by the manufacturers as activated and passivated forms.

Figure 5:
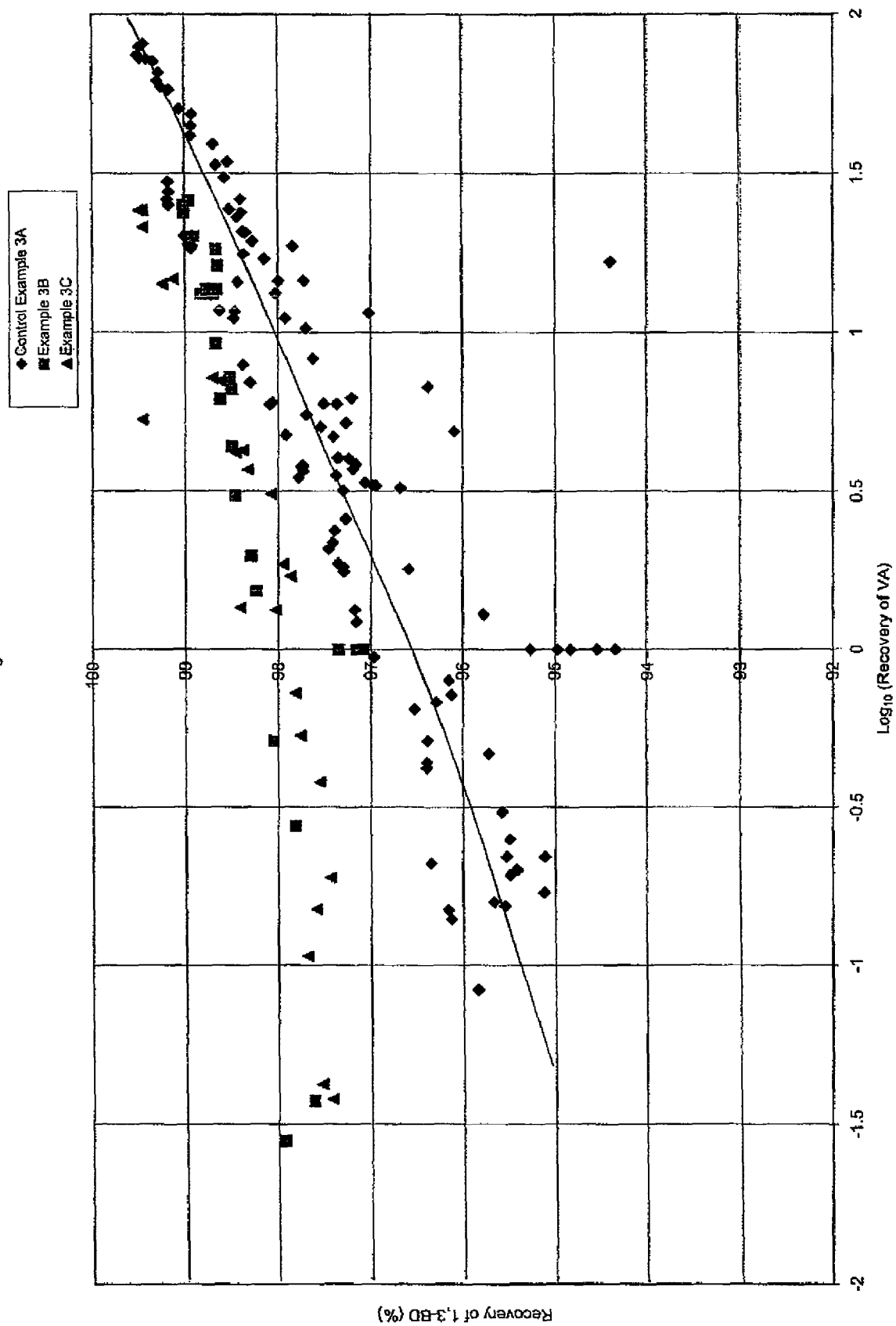
FIG. 5 is a chart comparing Control Example 3A with Invention Examples 3B and 3C for 1,3-butadiene recovery vs. vinyl acetylene recovery.
Figure 6:
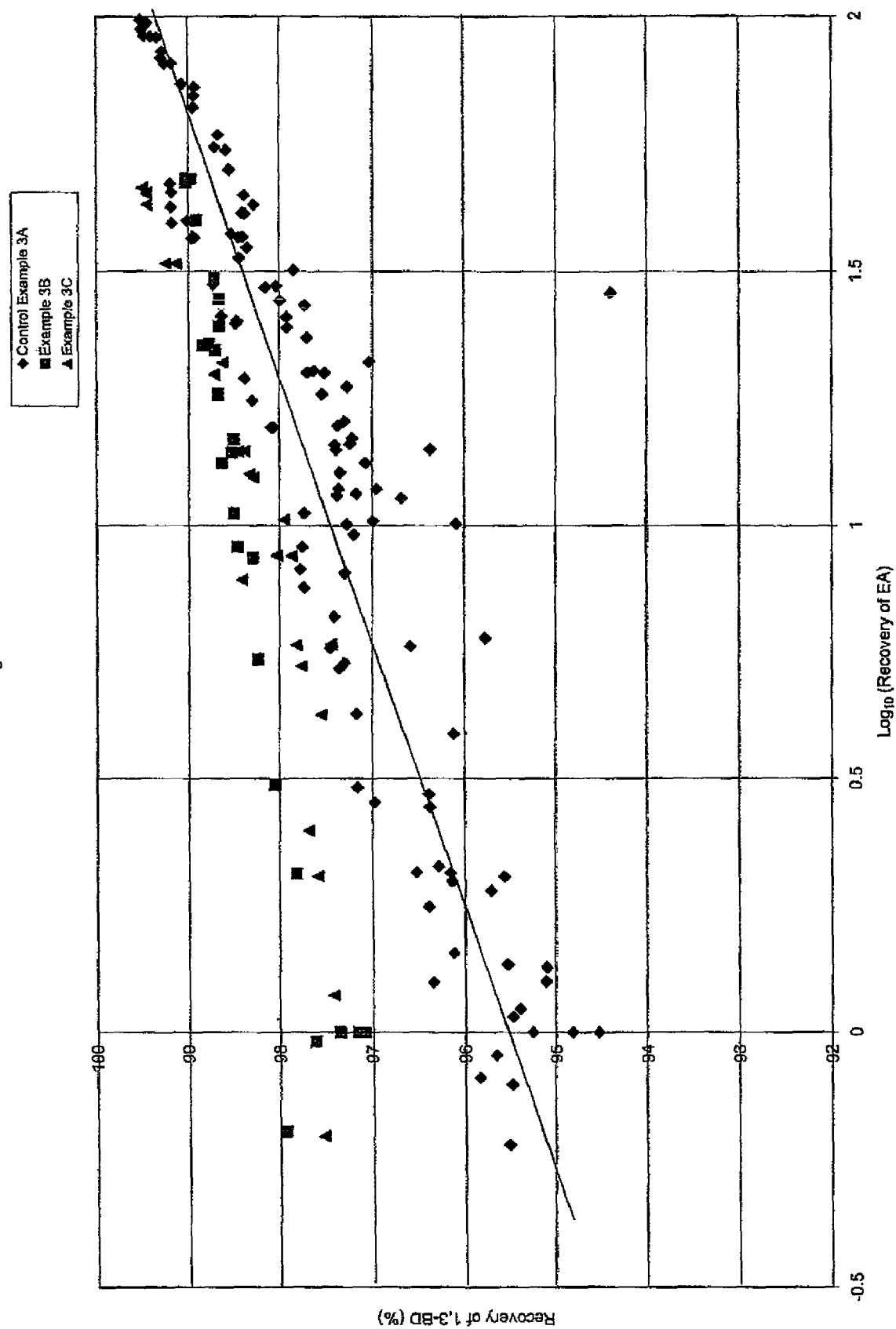
FIG. 6 is a chart comparing Control Example 3A with Invention Examples 3B and 3C for 1,3-butadiene recovery vs. ethyl acetylene recovery.

50 grams of each catalyst were tested for the selective hydrogenation of $C_4$ acetylenic impurities in a crude butadiene stream from a steam cracker. The tests were carried out in a similar way to Control Example 1A. The feed was comprised of 1.07 wt. % vinyl acetylene, 0.16 wt. % ethyl acetylene and 0.16 wt. % methyl acetylene, 71.40 wt. % 1,3-BD, 0.19 wt. % 1,2-BD, 14.59 wt. % butenes, etc. The selective hydrogenations were carried out at 6 ml/min of hydrocarbon feed and at 85 sccm/min of hydrogen flow rate at the beginning of the reaction, down to 50 sccm/min toward to the end of the run, under 108 psig total reactor pressure. The temperature of the hydrogenation was 120 to 128° F. at the end of the catalyst beds and about 88 to 99° F. at the beginning of the catalyst beds, respectively. The best performance was 95.3% recovery of 1,3-BD at 100% conversion of both VA and EA. The results are illustrated in FIGS. 5 and 6.

EXAMPLE 3B

Invention

The catalyst in this example was prepared by performing regular wet impregnation in the first step and spray-coating impregnation in the second step. The same calcined alumina (1100° C.) used in the Example 1C was used to prepare the nickel catalyst in this example.

A nickel nitrate solution was prepared by dissolving 94 g $NiNO_3 \cdot 6H_2O$ in 285 grams of water for the first impregnation. 300 grams of the same calcined alumina used in Example 1C were placed in a rotary impregnator and the above nickel nitrate solution was poured on the alumina support in the rotating impregnator. After cold rolling for 10 minutes, drying at about 200° C. was carried out by blowing hot air into the rotary impregnator. The dried impregnation product was calcined at 350° C. for 3 hours. Loading of nickel on alumina in this first impregnation was 5.95 wt. % based on the amount of nickel nitrate hexahydrate used. The observation of the calcined product from the first impregnation under a microscope indicates that nickel metal was dispersed more or less uniformly throughout the alumina spheres. Another nickel nitrate solution was prepared by dissolving 50 g $NiNO_3.6H_2O$ in 15 g water for the second impregnation. The second impregnation was carried out by spray-coating the nickel nitrate solution on the calcined product from the first impregnation in the rotary impregnator at ambient temperature over the period of about 15 minutes. After drying the impregnation product at about 200° C., the calcination was carried out at 350° C. for 2 hours. The amount of nickel deposited on the alumina support in the second impregnation step was 3.26 wt. % based on the amount of nickel nitrate used. The calculated net nickel content on the final product was 8.84 wt. %. Based on an observation made in a separate experiment, the second spray-coating impregnation deposited nickel metal in a layer of about 0.26 mm thickness on the alumina spheres. Therefore, about 82.8% of the total Ni loaded on the catalyst is deposited on the outer layer, which means 1.62 mg/m² Ni loading in the outer layer and 0.94 mg/m² Ni loading in the inner core region of the alumina spheres.

60 g of this catalyst were loaded in a vertically mounted up-flow stainless fixed bed reactor (1 inch diameter×20 inch long). The catalyst was activated at 250° F. in 300 cc/min gas flow of 33 volume % hydrogen gas in nitrogen for 1.5 hours, and then for 3 hours at 670° F. and for 3 hours at 770° F. by passing 350 cc per minute of pure hydrogen gas. The reactor was cooled to ambient temperature. The selective hydrogenation of acetylenic impurities in the same feed stream used in the Control Example 3A was carried out at 6 ml/min of hydrocarbon feed and at 55 sccm/min of hydrogen flow rate at the beginning of the reaction, down to 37 sccm/min toward to the end of the run, under 110 psig total reactor pressure. The temperature of the hydrogenation was 119 to 121° F. at the end of the catalyst bed and 81° to 89° F. at the beginning of the catalyst bed, respectively. The best quality product from this experiment contained 0 ppm VA and 0 ppm EA at 97.3% recovery of 1,3-butadiene. The result is illustrated in FIGS. 5 and 6 to show a superior performance of this example to those of the conventional nickel catalysts in the Control Example 3A.

EXAMPLE 3C

Invention

The catalyst in this example was prepared by performing regular wet impregnation in the first step and spray-coating impregnation in the second step. The alumina used to prepare the catalyst in this example was the alumina calcined at a lower temperature than the previous examples. The same gamma-alumina used in the Example 1C was calcined at 800° C. for 2 hours in air. This calcined alumina had 128 m$^2$/g BET surface area, 0.88 cm$^3$/g total N$_2$ pore volume, and 230 Å of average pore diameter. It had 0.55 g/cc ABD and 1.60 mm of average diameter of alumina spheres.

A nickel nitrate solution was prepared by dissolving 100 g NiNO$_3$.6H$_2$O in 285 grams of water for the first impregnation. 300 grams of the alumina calcined at 800° C. for 2 hours were placed in a rotary impregnator and the above nickel nitrate solution was poured on the alumina support in the rotating impregnator. After cold rolling for 10 minutes, drying at about 200° C. was carried out by blowing hot air into the rotary impregnator. The dried impregnation product was calcined at 350° C. for 3 hours. Loading of nickel on alumina in this first impregnation was 6.31 wt. % based on the amount of nickel nitrate hexahydrate used. The observation of the calcined product from the first impregnation under a microscope indicated that nickel metal was dispersed more or less uniformly throughout the alumina spheres. Another nickel nitrate solution was prepared by dissolving 66 g NiNO$_3$.6H$_2$O in 19.5 g water for the second impregnation. The second impregnation was carried out by spray-coating the nickel nitrate solution on the calcined product from the first impregnation in the rotary impregnator at ambient temperature over the period of about 15 minutes. After drying the impregnation product at about 200° C., the calcination was carried out at 350° C. for 2 hours. The amount of nickel deposited on the alumina support in the second impregnation step was 4.25 wt. % based on the amount of nickel nitrate used. The calculated net nickel content in the final product was 10.05 wt. %. Based on observation made in a separate experiment, the second spray-coating impregnation deposited nickel metal in a layer of about 0.335 mm thickness on the alumina spheres. Therefore, about 88.2% of the total Ni loaded on the catalyst is deposited on the outer layer, which means 0.958 mg/m$^2$ Ni loading in the outer layer and 0.526 mg/m$^2$ Ni loading in the inner core region of the alumina spheres.

60 grams of this catalyst were loaded in a vertically mounted up-flow stainless fixed bed reactor (1 inch diameter× 20 inch long). The catalyst was activated at 250° F. in 300 cc/min gas flow of 33 volume % hydrogen gas in nitrogen for 1.5 hours, and then for 3 hours at 670° F. and for 3 hours at 770° F. by passing 350 cc per minute of pure hydrogen gas. The reactor was cooled to ambient temperature. The selective hydrogenation of acetylenic impurities in the same feed stream used in the Control Example 3A was carried out at 6 ml/min of hydrocarbon feed and at 51 sccm/min of hydrogen flow rate at the beginning of the reaction, down to 37 sccm/min toward the end of the run, under 110 psig total reactor pressure. The temperature of the hydrogenation was 119 to 121° F. at the end of the catalyst bed and 81° to 89° F. at the beginning of the catalyst bed, respectively. The best quality product from this experiment contained 5 ppm VA and 10 ppm EA at 97.5% recovery of 1,3-butadiene. The result is illustrated in FIGS. 5 and 6 which show a superior performance of this example to those of the conventional nickel catalysts in the Control Example 3A.

EXAMPLE 4

Invention

The concept of two catalytic reaction zones is demonstrated in this example. A catalyst was prepared in the identical manner described in the Example 2C. A feed containing a low concentration of C$_4$ acetylenes in a mixed butadiene stream was tested over this catalyst as a second catalytic reaction zone in a fixed bed 40 grams of catalyst were loaded in a vertically mounted up-flow stainless fixed bed reactor (1 inch diameter×20 inch long). The catalyst was activated in the identical manner described in the Example 2C. The reactor was cooled to ambient temperature. The feed was comprised of 280 ppm wt vinyl acetylene, 120 ppm wt ethyl acetylene and 97 ppm wt % methyl acetylene, 49.18 wt % 1,3-BD, 190 ppm wt 1,2-BD, 28.05 wt % butenes, etc. The selective hydrogenation was carried out at 6 ml/min of hydrocarbon feed and at 7 sccm/min of hydrogen flow rate under 108 psig total reactor pressure. The temperature of the hydrogenation was 119° F. at the end of the catalyst bed and 77° F. at the beginning of the catalyst bed, respectively. The analysis product stream indicated the complete removal of all the acetylenic compounds in the feed. The recovery of 1,3-BD was 99.1%.

EXAMPLE 5

In this example, MAPD (methyl acetylene and propadiene) in a mixed C$_3$ olefin stream was removed by selective hydrogenation. Three catalysts (a commercial Pd catalyst and two Ni catalysts promoted with Cu and Cu/Pd) were tested to demonstrate the performance of this invention against Pd-based catalyst. Palladium-based catalysts are widely used to remove MAPD in crude C$_3$ streams in the commercial production of propylene.

Catalyst A (Comparison)

The catalyst was a commercial Pd (0.3 wt %) catalyst supported on alpha-alumina. The catalyst had eggshell type palladium deposition on 2.6 mm alumina extrudates. The amount of catalyst used was 40 grams. The catalyst was loaded in a stainless fixed bed reactor (1 inch diameter×20 inch long). The catalyst was activated at 400° F. in 300 sccm/min H$_2$ gas flow for 2 hrs.

Catalyst B; Ni Catalyst Promoted with Cu (Invention)

The catalyst was prepared in two-step spray impregnation technique. A mixed solution of nickel nitrate and copper nitrate was prepared by dissolving 86.5 g Ni(NO$_3$)$_2$.6H$_2$O and 2.5 g Cu(NO$_3$)$_2$.2.5H$_2$O in 26 grams of water for the impregnation. 300 grams of the 1100° C. calcined alumina used in the Example 1C was placed in a rotary impregnator, and the mixed solution was sprayed on the rolling alumina spheres with an atomizer at ambient temperature over a period of about 10 minutes. After drying the impregnation product at about 200° C. by blowing hot air into the rotary impregnator, the dried product was calcined at 350° C. for about 2 hours. Another mixed solution of nickel nitrate and copper nitrate was prepared for the second impregnation by dissolving 65 grains Ni(NO$_3$)$_2$.6H$_2$O and 1.8 grams Cu (NO$_3$)$_2$.2.5H$_2$O in 19.5 grams of water. The second impregnation was carried out on the calcined first impregnation product in the similar manner to the first impregnation. After drying at 200° C., the calcination at 380° C. was carried out for 2 hours. The amounts of nickel and copper deposited on the alumina support are 9.22 wt. % Ni and 0.35 wt. % Cu based on total amount of nickel nitrate and copper nitrate used. Examination of the calcined product by microscope indicated about 0.33 mm of the thickness of the peripheral mixed metal oxides layer on the alumina spheres. 50 grams of catalyst were loaded in a stainless fixed bed reactor (1 inch diameter×20 inch long). The catalyst was activated in the identical manner described in the Example 1C.

Catalyst C; Ni Catalyst Promoted with Cu and Pd (Invention)

The catalyst was prepared in two step impregnation technique. A mixed solution of nickel nitrate and copper nitrate was prepared by dissolving 106.5 g $Ni(NO_3)_2 \cdot 6H_2O$ and 4.5 g $Cu(NQ_3)_2 \cdot 2.5H_2O$ in 305 grams of water for the first impregnation. 300 grains of the 1100° C. calcined alumina used in the Example 1C was placed in a rotary impregnator. The mixed solution was poured on the rolling alumina spheres at ambient temperature in the rotary impregnator, and then the alumina is cold rolled for 10 minutes. After drying the impregnation product at about 200° C. by blowing hot air into the rotary impregnator, the dried product was calcined at 350° C. for about 2 hours. Another mixed solution of nickel nitrate, copper nitrate and palladium nitrate was prepared for the second impregnation by dissolving 60 g $Ni(NO_3)_2 \cdot 6H_2O$, 2.54 g $Cu(NO_3)_2 \cdot 2.5H_2O$ and 0.74 g $Pd(NO_3)_2 \cdot xH2O$ (42.8 wt % Pd) in 20.3 grams of water for the second impregnation. The second mixed solution was sprayed on rolling alumina spheres from the first impregnation product in a rotary impregnator with an atomizer at ambient temperature over a period of about 10 minutes. After drying at 200° C., calcination at 380° C. was carried out for 2 hours. The amounts of nickel, copper and palladium deposited on the alumina support are 9.98 wt. % Ni, 0.57 wt. % Cu and 0.09 wt. % Pd based on total amount of nickel nitrate, copper nitrate and palladium nitrate used. 50 grams of catalyst were loaded in a stainless fixed bed reactor (1 inch diameter×20 inch long). The catalyst was activated in the identical manner described in the Example 1C.

The performance of three catalysts was carried out with a feed composed of 94.6 wt. % propylene, 1.0 wt. % propane, 2.3 wt. % of methyl acetylene (MA), 0.9 wt. % propadiene (PD), 1.0% $C_2$ and 0.2 wt % $C_4$-$C_5S$. The flow direction of feed during the tests was up-flow. The results are listed in Table 3. The performance of the catalysts B and C is superior to the conventional palladium catalyst A.

TABLE 3

| Catalyst | A | B | C |
|---|---|---|---|
| Pressure, psig | 380 | 380 | 380 |
| Temperature, ° F. | | | |
| In | 71 | 137 | 140 |
| Out | 135 | 120 | 123 |
| HC Feed Rate, ml/min | 4.5 | 4.5 | 4.5 |
| H2 rate, sccm/min | 110 | 105 | 90 |
| WHSV | 3.4 | 2.7 | 2.7 |
| Propylene Yield, m % | 101.0 | 101.3 | 102.1 |
| MAPD Selectivity to C3H6, % | 34.7 | 43 | 67 |
| MAPD in product, wt. ppm | 54.9 MAPD | 12 MA | 0 |

EXAMPLE 6

In this example, the deposition of heavy polymers on a Ni catalyst of the present invention and a commercial Ni catalyst was investigated. A catalyst (Catalyst D) was prepared in two-step spray impregnation technique according to the technique disclosed in this invention as follows.

A nickel nitrate solution was prepared by dissolving 86.5 g $Ni(NO_3)_2 \cdot 6H_2O$ in 26 grams water for the first impregnation. 300 grams of the 1100° C. calcined alumina used in the Example 1C was placed in a rotary impregnator, and the solution was sprayed on the rolling alumina spheres with an atomizer at ambient temperature over a period of about 10 minutes. After drying the impregnation product at about 200° C. by blowing hot air into the rotary impregnator, the dried product was calcined at 350° C. for about 2 hours. Another nickel nitrate solution was prepared for the second impregnation by dissolving 47.3 $Ni(NO_3)_2 \cdot 6H_2O$ in 14.2 grams of water. The second impregnation was carried out on the calcined first impregnation product in a manner similar to the first impregnation. After drying at 200° C., calcination was carried out for 2 hours at 380° C. The amount of nickel deposited on the alumina support are 8.26 wt. % Ni based on total amount of nickel nitrate used. The examination of the calcined product under a microscope indicated about 0.33 mm of the thickness of the mixed metal oxides layer on the alumina spheres.

40 grams catalysts were loaded in a stainless fixed bed reactor (1 inch diameter×20inch long). The catalyst was activated in the identical manner described in the Example 1C.

40 grams the same commercial Ni catalyst (KL6564-TL1.2) used in control Example 1B were loaded in another stainless fixed bed reactor (1 inch diameter×20 inch long). The catalyst was activated in the identical manner described in the Example Control Example 1B.

Deposition of heavy polymers on both catalysts was investigated on both catalysts by carrying out selective hydrogenation of C4 acetylenic compounds in crude butadiene streams under various conditions for over 4000 hours. Carbon contents on both spent catalyzed. The result is listed in Table 4. The carbon content on Catalyst D is extremely low compared with KL6564.

TABLE 4

| Catalyst | Catalyst D | KL6564 |
|---|---|---|
| Total run hours | 4046 | 4094 |
| Carbon wt. % on spent catalyst | 1.78 | 29.5 |

The invention claimed is:

1. A supported nickel selective hydrogenation catalyst composition comprising 3 to 20 wt. % Ni and a promoting or modifying amount of one or more elements selected from the group consisting of Cu, Pd, Re, Zn, Mg, Mo and Bi deposited on a porous support comprising more than about 60% of said Ni deposited on the outer periphery of said porous support.

2. The catalyst according to claim 1 wherein the porous support has a BET surface area of greater than 10 $m^2$/g.

3. The catalyst according to claim 1 wherein the porous support has an average pore diameter from about 100 Å to about 450 Å.

4. The catalyst according to claim 1 wherein the porous support has a total nitrogen adsorption pore volume from about 0.4 cc/g to about 1 cc/g.

5. The catalyst according to claim 1 wherein the porous support has a BET surface area from about 20 $m^2$/g to about 150 $m^2$/g, an average pore diameter from about 100 Å to about 450 Å and a total nitrogen adsorption pore volume from about 0.4 cc/g to about 1 cc/g.

* * * * *